: US 9,347,914 B2
(45) Date of Patent: May 24, 2016

(12) United States Patent
Tabuchi et al.

(54) GAS SENSOR

(71) Applicant: NGK SPARK PLUG CO., LTD., Nagoya-shi, Aichi (JP)

(72) Inventors: Daiki Tabuchi, Aichi (JP); Hidekazu Kato, Ichinomiya (JP); Yasuhiro Fujita, Kaizu (JP); Mitsuru Sugihara, Iwakura (JP); Takayoshi Atsumi, Konan (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 146 days.

(21) Appl. No.: 14/234,242

(22) PCT Filed: Oct. 26, 2012

(86) PCT No.: PCT/JP2012/006872
§ 371 (c)(1),
(2) Date: Jan. 22, 2014

(87) PCT Pub. No.: WO2013/065270
PCT Pub. Date: May 10, 2013

(65) Prior Publication Data
US 2014/0190829 A1    Jul. 10, 2014

(30) Foreign Application Priority Data

Nov. 4, 2011 (JP) ................................. 2011-242549
Sep. 20, 2012 (JP) ................................. 2012-206914

(51) Int. Cl.
*G01N 27/407*    (2006.01)
(52) U.S. Cl.
CPC ................................. *G01N 27/4077* (2013.01)

(58) Field of Classification Search
CPC .................................................... G01N 27/407
See application file for complete search history.

(56) References Cited

U.S. PATENT DOCUMENTS 4,802,369 A * 2/1989 Morii ................. G01N 27/4077
204/424
5,271,821 A * 12/1993 Ogasawara ........ G01N 27/4077
204/428

(Continued)

FOREIGN PATENT DOCUMENTS

JP    53-103785 U    8/1978
JP    8-193971 A    7/1996

(Continued)

OTHER PUBLICATIONS

International Search Report for PCT/JP2012/006872 dated Dec. 11, 2012.

(Continued)

*Primary Examiner* — Jennifer Dieterle
(74) *Attorney, Agent, or Firm* — Sughrue Mion, PLLC

(57)    ABSTRACT

A gas sensor includes a metal shell, a gas sensor element held in the metal shell, a metal portion arranged between a flange portion of the gas sensor element and a seat portion of the metal shell and a porous thermal spray layer formed on the gas sensor element. When viewed in cross section along the direction of an axis of the gas sensor, a corner of the metal portion axially overlaps in position with or radially outwardly protrudes from an outer surface of a part of the thermal spray layer located on a side surface of the flange portion and is brought into contact with the seat portion. A rear end-facing surface of the metal portion is brought into contact with an outer surface of the thermal spray layer at a position radially inside the side surface of the flange portion.

5 Claims, 12 Drawing Sheets

(56) References Cited

U.S. PATENT DOCUMENTS

| | | | |
|---|---|---|---|
| 5,670,032 A | 9/1997 | Friese et al. | |
| 5,688,390 A | 11/1997 | Yamauchi et al. | |
| 5,698,084 A | 12/1997 | Weyl et al. | |
| 6,096,181 A | 8/2000 | Friese et al. | |
| 6,446,489 B2 * | 9/2002 | Asai | G01N 27/4077 73/31.05 |
| 7,211,222 B2 | 5/2007 | Satou et al. | |
| 7,222,516 B2 * | 5/2007 | Nishio | G01N 27/407 73/23.31 |
| 2003/0116435 A1 | 6/2003 | Satou et al. | |
| 2005/0224349 A1 * | 10/2005 | Hirasawa | G01N 27/407 204/431 |
| 2010/0059374 A1 * | 3/2010 | Shiono | G01N 27/4073 204/424 |
| 2010/0101950 A1 * | 4/2010 | Sakurai | G01N 27/4067 204/424 |

FOREIGN PATENT DOCUMENTS

| | | |
|---|---|---|
| JP | 09-500729 A | 1/1997 |
| JP | 09-501776 A | 2/1997 |
| JP | 2000-502456 A | 2/2000 |
| JP | 2000-502457 A | 2/2000 |
| JP | 2002-323473 A | 11/2002 |
| JP | 2003-114210 A | 4/2003 |
| JP | 2007-322134 A | 12/2007 |

OTHER PUBLICATIONS

Office Action (Notification of Reasons for Rejection) dated Feb. 22, 2016 for corresponding Japanese Patent Application No. 2012-206914.

* cited by examiner (a)

(b)

GAS SENSOR

CROSS REFERENCE TO RELATED APPLICATIONS

This application is a National Stage of International Application No. PCT/JP2012/006872 filed Oct. 26, 2012, claiming priority based on Japanese Patent Application Nos. 2011-242549 filed Nov. 4, 2011 and 2012-206914 filed Sep. 20, 2012, the contents of all of which are incorporated herein by reference in their entirety.

TECHNICAL FIELD

The present invention relates to a gas sensor having a gas sensor element for detecting the concentration of a gas under measurement.

BACKGROUND ART

As a gas sensor for detecting the concentration of a specific gas component (such as oxygen or NOx) in an exhaust gas of an automotive vehicle etc., there is known a gas sensor having a gas sensor element equipped with a solid electrolyte body. One such type of gas sensor is known, including a gas sensor element having a cylindrical element body and an outer electrode formed on an outer surface of the element body and a metal shell surrounding a radially outer circumference of the gas sensor element to hold therein the gas sensor element (see e.g. Patent Document 1).

As shown in FIG. 12, for example, a gas sensor element 3 has an element body 3s formed with a radially outwardly protruding flange portion 3a; and a metal shell 1000 has a tapered seat portion 1000e formed on an inner surface thereof to hold the gas sensor element 3 by indirect contact of a front end-facing surface 3af of the flange portion 3a with the seat portion 1000e. An annular plate-shaped metal packing 12 is arranged between the seat portion 1000e of the metal shell 100 and the flange portion 3a of the gas sensor element 3 (see FIG. 12(a)) and is deformed along the seat portion 1000e by crimping a rear end portion of the metal shell 1000, with a filling material 6 filled between the gas sensor element 3 and the metal shell 1000, and thereby allowing the filling material 6 to push the flange portion 3a of the gas sensor element 3 toward the front end side (see FIG. 12(b)).

PRIOR ART DOCUMENTS

Patent Documents

Patent Document 1:
Japanese Laid-Open Patent Publication No. 2003-114210 (FIG. 11)
Patent Document 2:
Japanese Laid-Open Patent Publication No. 2007-322134 (FIGS. 2 and 4)

SUMMARY OF THE INVENTION

Problems to be Solved by the Invention

In the gas sensor of Patent Document 1, however, an outside diameter of a corner 12j of the metal packing 12 is smaller than an outside diameter of the seat portion 1000e of the metal shell 1000 as shown in FIG. 12(b) so that, when the metal packing 12 is deformed along the seat portion 1000e of the metal shell 1000, there occurs a radial displacement of the metal packing 12. Herein, the corner 12j of the metal packing 12 refers to a corner between a front end-facing surface 12f of the metal packing 12 and a side surface 12y of the metal packing 12. As a solution to such a problem, it is conceivable to bring the outside diameter of the metal packing 12 closer to the outside diameter of the seat portion 1000e of the metal shell 100 such that the metal packing 12 can be prevented from radial displacement during deformation of the metal packing 12 along the seat portion 1000e of the metal shell 100.

By the way, it is effective to cover an outer electrode of the gas sensor element 3 by a thermal spray coating (thermal spray layer 5) for the purpose of protecting the outer electrode from a poisoning substance etc. in a gas under measurement. The thermal spray layer 5 needs to be formed from a front end portion of the element body 3s to at least a side surface 3as of the flange portion 3a via the front end-facing surface 3af of the flange portion 3a (see FIG. 12(b)). This is because of, as an outer lead (not shown) is formed on the front end-facing surface 3af and side surface 3as of the flange portion 3a for connection of the outer electrode to an external circuit, preventing a short circuit between the lead and the metal shell 1000 and avoiding superimposition of noise onto the output of the gas sensor.

By the formation of the thermal spray layer 5 up to the side surface 3as of the flange portion, there arises a possibility of separation of the thermal spray layer 5 from the side surface 3as of the flange portion 3a in the case where the outside diameter of the metal packing 12 is made closer to the outside diameter of the seat portion 1000e of the metal shell 1000 as mentioned above. The reason for this is assumed as follows. At the time of placing the metal packing 12 on the seat portion 1000e of the metal shell 1000, a part of the thermal spray layer 5 located in the vicinity of a corner 3ac between the side surface 3as and front end-facing surface 3af of the flange portion 3a (more specifically, a part of the thermal spray layer 5 located radially outside of the front-facing surface 3af of the flange portion 3a) comes into contact with the metal packing 12. In such a state, crimping stress is exerted on the part of the thermal spray layer 5 located on the side surface 3as of the flange portion 3a in a direction along the side surface 3as of the flange portion 3a at the time of crimping the rear end portion of the metal shell 1000. As a result, there occurs a separation at the interface between the side surface 3as of the flange portion 3a and the thermal spray layer 5. Although the thermal spray layer 5 is also formed on the front end-facing surface 3af of the flange portion 3a and subjected to crimping stress at the time of crimping the rear end portion of the metal shell 1000, this stress is exerted on the thermal spray layer 5 in a direction intersecting the front end-facing surface 3af of the flange portion 3a (as a compression stress) so that there does not occur a separation at the interface between the front end-facing surface 3af of the flange portion 3a and the thermal spray layer 5.

There is also known a gas sensor in which a metal shell has a seat portion for receiving a flange portion of a gas sensor element such that the seat portion has two step surfaces: a main seat surface and an outer seat surface extending radially outwardly from the main seat surface to retain thereon an outer circumferential edge portion of a metal packing (see e.g. Patent Document 2). This gas sensor is manufactured by placing the metal packing on the outer seat surface of the metal shell, accommodating the gas sensor element in the metal shell, and then, pressing the gas sensor element toward the front end side so as to deform the metal packing along the main seat surface of the metal shell. The metal packing can be thus prevented from radial displacement relative to the step portion of the metal shell. Further, the metal packing has an inner portion tapered and constricted toward the front end side and brought into contact with the main seat surface and an outer portion bent into a horizontal direction from an outer edge of the inner portion.

Even when a thermal spray layer is formed on the gas sensor element in the gas sensor of Patent Document 2, there is a gap left between a part of the thermal spray layer located in the vicinity of a corner of the flange portion and the outer portion of the metal packing as the seat portion of the metal shell is formed with a double-step structure and as the outer portion of the metal packing is bent into the horizontal direction as mentioned above. The thermal spray layer can be thus prevented separation from a side surface of the flange portion. However, it is necessary to adopt a process operation for forming two step surfaces on the flange portion of the metal shell (i.e. it is necessary to perform not only forging process but also cutting process etc. for forming two step surfaces on the flange portion) in the gas sensor of Patent Document 2. The adoption of such a process operation causes much expense in time and effort. It is also necessary, at the time of pressing the gas sensor element toward the front end side by crimping the rear end portion of the metal shell, to perform the pressing process in two steps corresponding to the respective two step surfaces of the metal shell. The manufacturing of the gas sensor becomes time-consuming due to such pressing process.

It is therefore an object of the present invention to provide a gas sensor that has a metal shell, a gas sensor element with a flange portion and a thermal spray layer and can avoid separation of the thermal spray layer from a side surface of the flange portion of the gas sensor element, while preventing a radial displacement of the metal member, without complicating production of the metal shell.

Means for Solving the Problems

As a solution to the above problems, there is provided according to the present invention a gas sensor, comprising: a gas sensor element extending in an axis direction of the gas sensor and including a bottomed cylindrical element body and an outer electrode, the element body being exposed to a gas under measurement at a front end side thereof and opened at a rear end side thereof and having a radially outwardly protruding flange portion, the outer electrode being formed on an outer surface of a front end portion of the element body located front of the flange portion; a cylindrical metal shell radially outwardly surrounding the gas sensor element and having, on an inner surface thereof, a seat portion tapered and inclined toward the front end side so as to face a front end-facing surface of the flange portion; and an annular metal portion arranged between the front end-facing surface of the flange portion and the seat portion, wherein the gas sensor further comprises a porous thermal spray layer formed on a region from the front end portion of the element body via the front end-facing surface to at least a side surface of the flange portion so as to cover the outer electrode; and wherein, when viewed in cross section along the axis direction, a corner connecting a radially outer side surface of the metal portion and a front end-facing surface of the metal portion is formed so as to axially overlap in position with or radially outwardly protrude from an outer surface of a part of the thermal spray layer located on the side surface of the flange portion and is brought into contact with the seat portion, and a rear end-facing surface of the metal portion is brought into contact with an outer surface of a part of the thermal spray layer located on the front end-facing surface of the flange portion at a position radially inside the side surface of the flange portion.

In this gas sensor, the corner between the radially outer side surface and front end-facing surface of the metal portion axially overlaps in position with or radially outwardly protrudes from the outer surface of the part of the thermal spray layer located on the side surface of the flange portion so that the radial space between the metal portion and the metal shell can be made smaller. This makes it less likely that the metal portion will be radially displaced in position relative to the metal shell.

Further, the seat portion of the metal shell with which the metal portion is brought into contact is formed to define a single tapered surface that is inclined (constricted) directly from the inner side surface of the metal shell toward the front end side. This makes it possible to facilitate the production of the metal shell without the need to form a plurality of step surfaces on the inner surface of the metal shell. This also makes it possible, at the time of pressing the gas sensor element toward the front end side by crimping the rear end portion of the metal shell, to eliminate the need to perform a plurality of pressing steps corresponding to the respective step surfaces of the metal shell and to press the gas sensor element in one step for reduction of processing time.

Furthermore, the rear end-facing surface of the metal portion is brought into contact with the outer surface of the part of the thermal spray layer located on the front end-facing surface of the flange portion at a position radially inside the side surface of the flange portion so that there is a gap left between the part of the thermal spray layer located in the vicinity of the corner and the metal portion. This makes it possible to, in the case where an outside diameter of the metal portion is made closer to an outside diameter of the seat portion of the metal shell, keep the metal portion from contact with the part of the thermal spray layer located in the vicinity of the corner and prevent separation of the thermal spray layer from the side surface of the flange portion even when crimping stress is exerted on the part of the thermal stray layer located on the side surface of the flange portion in a direction along the side surface of the flange portion at the time of pressing the gas sensor element toward the front end side by crimping the rear end portion of the metal shell.

The gas sensor may be configured such that the side surface and front end-facing surface of the flange portion are connected by a curved surface or a plain surface.

The gap can be formed between the part of the thermal spray layer located in the vicinity of the corner and the metal portion, i.e., the rear end-facing surface of the metal portion can be brought into contact with the outer surface of the part of the thermal spray layer located on the front end-facing surface of the flange portion at the position radially inside the side surface of the flange portion, only by adjusting the shape of the corner of the flange shape to a curved surface or a plane surface.

The gas sensor may be configured such that, in a region radially outside the contact of the metal portion and the outer surface of the thermal stray layer, an angle formed between the rear end-facing surface of the metal portion and the axis direction is larger than an angle formed between the outer surface of the thermal spray layer and the axis direction.

In this gas sensor, the gap can be formed between the part of the thermal spray layer located in the vicinity of the corner and the metal portion, i.e., the rear end-facing surface of the metal portion can be brought into contact with the outer surface of the part of the thermal spray layer located on the front end-facing surface of the flange portion at the position radially inside the side surface of the flange portion even when the metal portion has a uniform thickness and an ordinary shape.

The gas sensor may be configured such that the metal portion is reduced in thickness toward the radially outside.

The gap can be formed between the part of the thermal spray layer located in the vicinity of the corner and the metal portion, i.e., the rear end-facing surface of the metal portion can be brought into contact with the outer surface of the part of the thermal spray layer located on the front end-facing surface of the flange portion at the position radially inside the side surface of the flange portion, only by reducing the thickness of the metal portion toward the radially outside.

The gas sensor may have a protector portion formed integral with the metal portion so as to extend from the metal portion toward the front end side and accommodate therein the gas sensor element.

As the protector portion is formed integral with the metal portion so as to accommodate therein the gas sensor element, the parts count of the gas sensor can be reduced for productivity improvement and cost reduction.

Effects of the Invention

It is possible according to the present invention to avoid separation of the thermal spray layer from the side surface of the flange portion of the gas sensor element, while preventing radial positional displacement of the metal member, without complicating production of the metal shell.

DETAILED DESCRIPTION OF EMBODIMENTS

Exemplary embodiments of the present invention will be described below.

Figure 1:
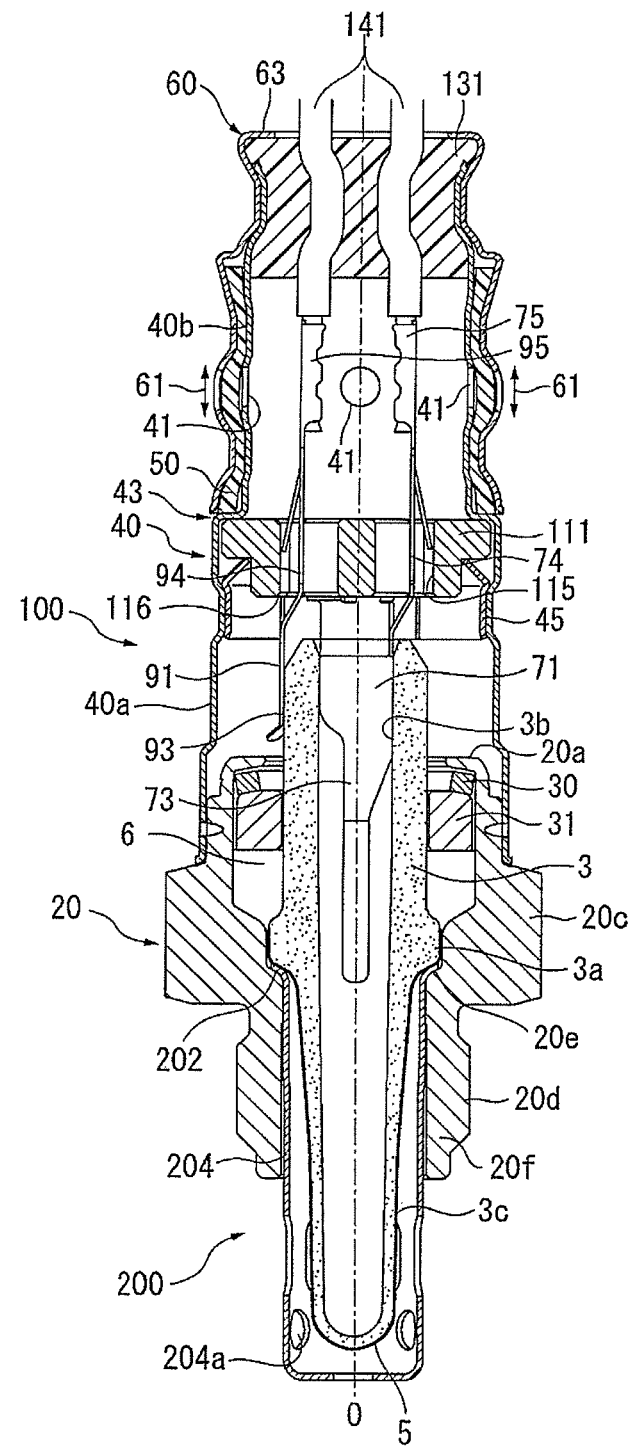
FIG. 1 is a cross-section view of a gas sensor, taken along the direction of an axis of the gas sensor, according to a first embodiment of the present invention.

FIG. 1 is a cross-section view of a gas sensor 100, taken along the direction of an axis O of the gas sensor 100 (the direction from the front end to the rear end), according to a first embodiment of the present invention. In the first embodiment, the gas sensor 100 is an oxygen sensor for use by insertion into an exhaust pipe of an automotive vehicle so as to expose a front end portion (protector portion 204 side) thereof to exhaust gas and detect the concentration of oxygen in the exhaust gas. Herein, the bottom side of FIG. 1 (protector portion 204 side) is referred to as the front end side of the gas sensor 100; and the top side of FIG. 1 is referred to as the rear end side of the gas sensor 100.

The gas sensor 100 includes a metal shell 20 (as a housing) and a gas sensor element 3 held in the metal shell 20. The gas sensor element 3 is a known type of oxygen gas sensor element having an oxygen concentration cell structure in which a pair of electrodes is arranged on an oxygen-ion conducting solid electrolyte body for outputting a detection value responsive to the amount of oxygen. More specifically, the gas sensor element 3 has a bottomed cylindrical element body 3s made of a solid electrolyte and tapered so as to decrease in diameter toward the front end (see FIG. 2), an inner electrode 3b formed on an inner circumferential surface of the element body 3s and an outer electrode 3c formed on an outer circumferential surface of the element body 3s. A reference gas atmosphere is created in an inner space of the gas sensor element 3. In this configuration, the gas sensor element 3 detects oxygen gas upon contact of the gas under measurement with the outer surface of the gas sensor element 3.

A radially outwardly protruding flange portion 3a is formed on an axially middle part of the gas sensor element 3. On the other hand, a tapered seat portion 20e is formed on a front end part of an inner circumferential surface of the metal shell 20 so as to decrease in diameter and become constricted inwardly toward the front end side. An annular metal portion 202 of a protector 200 is arranged between the flange portion 3a and the seat portion 20e and is connected to a protector portion 204 (explained in detail later) of the protector 200. The gas sensor element 3 is held in the metal shell 20 by inserting the gas sensor element 3 into the metal shell 20, the flange portion 3a of the gas sensor 3 into contact with the metal portion 202 of the protector 200 and thereby indirectly brining the flange portion 3a into contact with the seat portion 20e from the rear end side.

Figure 2:
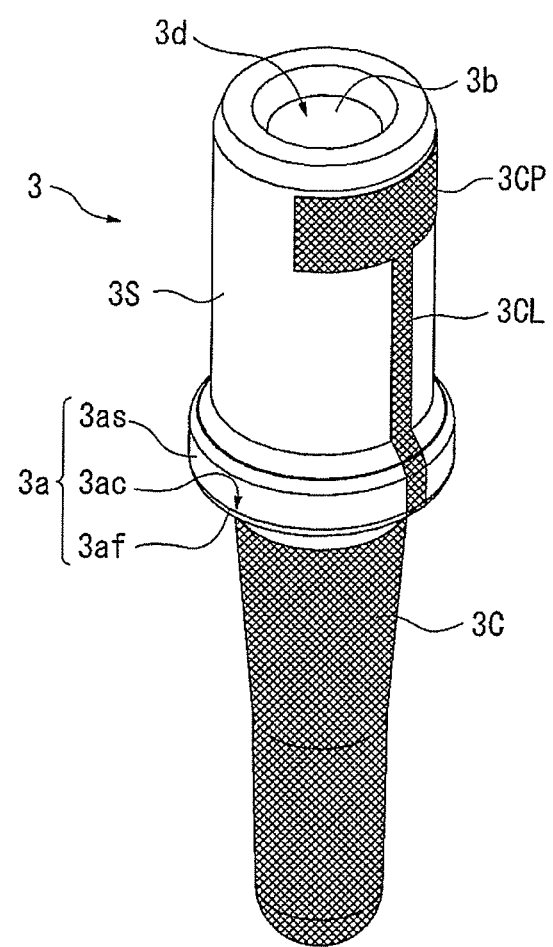
FIG. 2 is a perspective view of a gas sensor element formed with an outer electrode.

As shown in FIG. 2, the flange portion 3a of the gas sensor element 3 has a front-facing surface 3af directed toward the front end side of the gas sensor element 3, a side surface 3as and a corner 3ac connecting the front end-facing surface 3af and the side surface 3as. In the gas sensor element 3, the outer electrode 3c is formed on a part of the outer circumferential surface of the element body 3s located front of the flange portion 3a. A lead 3cL is formed so as to extend from the outer electrode 3c toward the rear end side and is connected to an electrode pad 3cp on a rear end part of the outer circumferential surface of the element body 3s.

Figure 3:
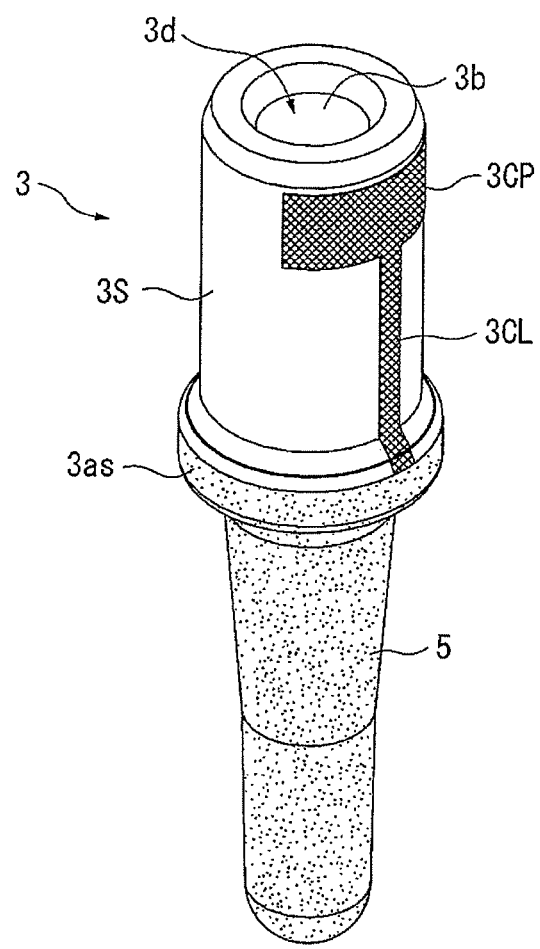
FIG. 3 is a perspective view of a thermal spray layer formed on the gas sensor element.

For the purpose of protecting the outer electrode 3c from a poisoning substance in the gas under measurement, a porous thermal spray layer 5 is formed on a region extending from the front end portion 3af the gas sensor element 3 (element body 3s) to at least the side surface 3as of the flange portion 3a via the front end-facing surface 3af of the flange portion 3a such that the outer electrode 3c (as a detection electrode) is covered by the thermal spray layer 5 as shown in FIG. 3. In order to prevent a short circuit between the lead 3cL, which is located on the front end-facing surface 3af and side surface 3as of the flange portion 3a, and the metal shell 20 and to avoid superimposition of noise onto the sensor output, the thermal spray layer 5 needs to be formed continuously from the front end portion of the element body to at least the side surface 3as of the flange portion 3a via the front end-facing surface 3af of the flange portion 3a. By contrast, at least the electrode pad 3cp needs to be kept exposed, without being covered by the thermal spray layer 5, for electrical connection to the aftermentioned outer terminal 91.

Referring back to FIG. 1, the metal portion 202 and the protector portion 204 are formed integrally in the protector 200. The metal portion 202 is tapered and constricted toward the front end side and is brought into contact with the seat portion 20e. The protector portion 204 is cylindrical in shape and extends from a front end of the metal portion 202 toward the front end side. The metal portion 202 is engaged between the flange portion 3a and the seat portion 20e. The protector portion 204 protrudes from a front end portion 20f of the metal shell 20 so as to accommodate therein a front end portion of the gas sensor element 3, which also protrudes from the front end portion 20f of the metal shell 20, and has a bottomed cylindrical shape with a front end side thereof closed and a plurality of holes 204a formed therein to introduce the exhaust gas to the inside of the protector portion 204.

The protector 200 can be made of e.g. nickel, nickel alloy or stainless steel (such as SUS430).

A cylindrical seal material (talc powder) 6 is filled in a radial space between the part of the gas sensor element 3 and the metal shell 20, both of which are located rear of the flange portion 3a. A cylindrical insulating member (ceramic sleeve) 31 is arranged on a rear end side of the seal material 6. A metal ring (stainless plain washer) 30 is arranged on a rear end side of the insulating member 31. When a crimp portion 20a is formed by inwardly crimping a rear end portion of the metal shell 20, the insulating member 31 is pushed toward the front end side to compress the seal material 6 and thereby fix the insulating member 31 and the seal material 6 and, at the same time, seal the space between the gas sensor element 3 and the metal shell 20.

A radially outwardly protruding polygonal flange portion 20c is also formed on an axially middle part of the metal shell 20 so as to engage with e.g. a hexagonal wrench. A male thread portion 20d is formed on a part of the outer surface of the metal shell 20 between the flange portion 20c and the front end portion 20f. A gasket (not shown) is fitted around a step portion between a front end face of the flange portion 20 and a rear end of the male thread portion 20d so as to prevent gas leakage in the state of mounting the gas sensor to the exhaust pipe. The front end portion of the gas sensor element 3 is exposed inside the exhaust gas, by fitting the male thread portion 20d of the metal shell 20 in a screw hole of the exhaust pipe, for detection of the gas under measurement (exhaust gas).

A cylindrical metallic outer tube 40 is joined to the rear end portion of the metal shell 20 so as to cover a rear end portion of the gas sensor element 3. The outer tube 40 has a front end portion 40a connected to the metal shell 20, a rear end portion 40b made smaller in diameter than the front end portion 40a and a step portion 43 located between the front end portion 40a and the rear end portion 40b.

A cylindrical insulating separator 111 is arranged inside the front end portion 40a of the outer tube 40 and is formed with two insertion holes 115 and 116.

Inner and outer terminals 71 and 91 have plate-shaped base portions 74 and 94 inserted into the insertion holes 115 and 116 and connection end portions 75 and 95 formed on rear ends of the base portions 74 and 94 and connected by crimping to leads 141, respectively.

The separator 111 is thus held in the outer tube 40 by contact of a rear end face of the separator 111 with the step portion 43 and by contact of a front end face of the separator 111 with a holder member 45. The holder member 45 is located front of the separator 111 and fixed in the outer tube 40 by crimping the front end portion 40a of the outer tube 40.

The inner terminal 71 also has an insertion portion 73 connected to the plate-shaped base portion 74 and fitted in a cylindrical hole 3d of the gas sensor element 3. The insertion portion 73 is cylindrical in shape and is electrically connected to the inner electrode 3b inside the gas sensor element 3. The outer terminal 91 also has a cylindrical portion 93 connected to the plate-shaped base portion 94 and fitted around the gas sensor element 3. The cylindrical portion 93 is cylindrical in shape and is electrically connected to the outer electrode 3c (more specifically, electrode pad 3cp) outside the gas sensor element 3.

A cylindrical grommet 131 is fitted by crimping in the rear end portion 40b of the outer tube 40 and formed with two insertion holes so that the leads 141 are led out to the outside from the insertion holes, respectively. A rear end portion of the grommet 131 is flanged and enlarged in diameter. The grommet 131 is placed in position by disposing this enlarged-diameter part on the rear end of the outer tube 40. As the grommet 131, there can be used a rubber cap made of silicon rubber, fluoro rubber etc.

Four circumferentially evenly spaced first air holes 41 are opened at positions front of the grommet 131 on a lateral surface of the rear end portion 40b of the outer tube 40 (although only three air holes 41 are shown in FIG. 1). An annular air-permeable filter 50 is fitted racially around the rear end portion 40b of the outer tube 40 so as to close the first air holes 41. Further, a cylindrical metallic protection tube 60 is fitted radially around the filter 50. Four circumferentially evenly spaced second air holes 61 are opened on a lateral surface of the protection tube 60 (although only two air holes 61 are shown in FIG. 1). The outside air can be thus introduced to the inside of the outer tube 40 through the filter 50. The filter 50 is held between the outer tube 40 and the protection tube 60 by crimping the outer tube 40 and the protection tube 60 at positions front and rear of the first and second air holes 41 and 61. The filter 50 has a porous structural body made of resin such as fluoro resin and shows water repellency so as to introduce a reference gas (outside air) into the inner space of the sensor element 3 without the entry of water from the outside.

A rear end of the protection tube 60 is bent radially inwardly and thereby placed on a rear end face of the grommet 131. A through hole 63 is formed in the center of the rear end of the protection tube 60 so that the leads 141 are led out to the outside from the through hole 63. A rear end portion of the protection tube 60 is fixed by crimping to the crimped regions of the rear end portion 40b of the outer tube 40. Namely, the grommet 131 is arranged in the outer tube 40 by simultaneously crimping the protection tube 60 and the outer tube 40.

Next, the characteristic features of the present invention will be explained below with reference to FIG. 4.

Figure 4:
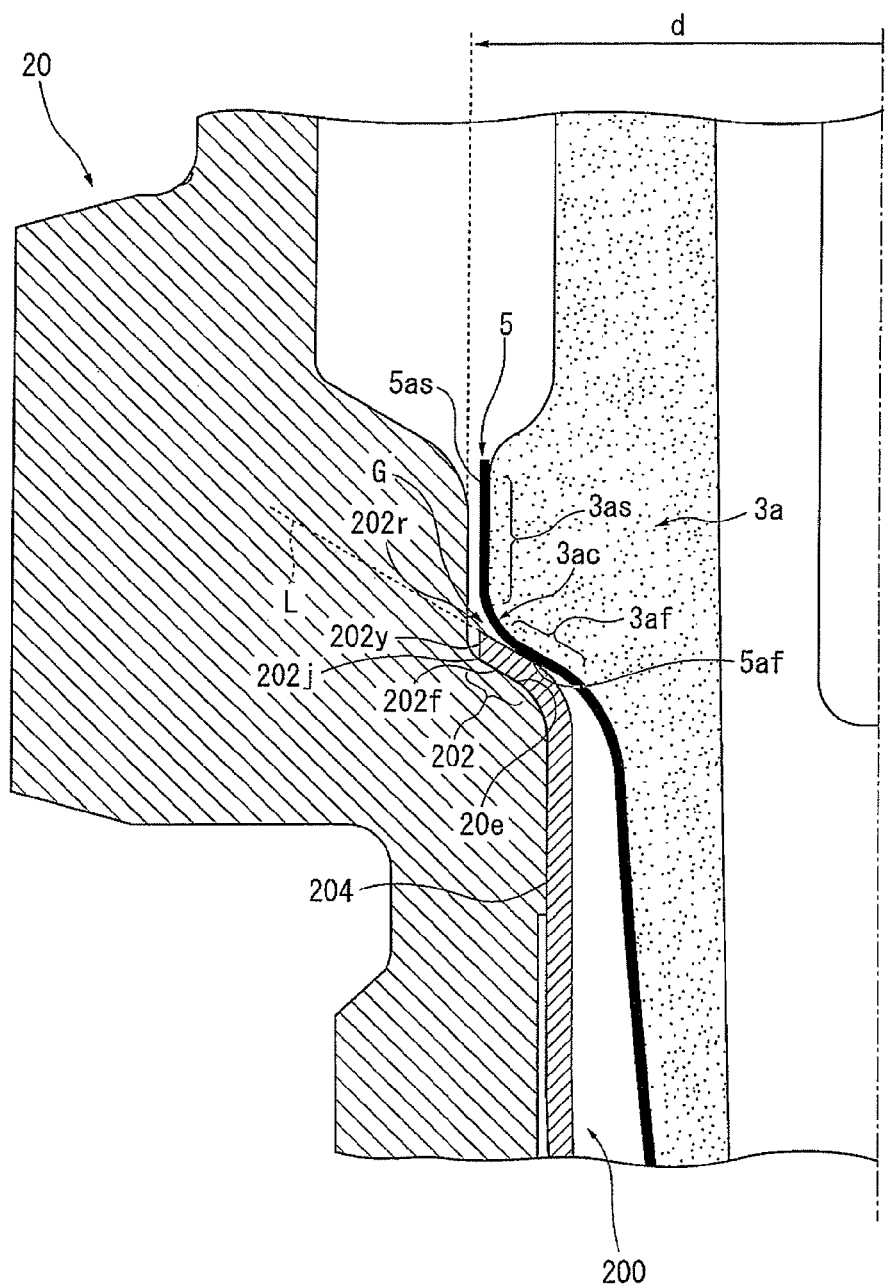
FIG. 4 is a schematic enlarged view of part of FIG. 1, showing a metal portion in the gas sensor according to the first embodiment of the present invention.

FIG. 4 is a schematic enlarged view of part of FIG. 1. In the first embodiment, an outer side surface 202y of the metal portion 202 of the protector 200 axially overlaps in position with an outer surface 5as of a part of the thermal spray layer 5 located on the side surface 3as of the flange portion 3a (that is, the outer side surface 202y of the metal portion 202 and the outer surface 5as of the thermal spray layer 5 are radially in the same position). In other words, a corner 202j connecting the outer side surface 202y and front end-facing surface 202f of the metal portion 202 axially overlaps in position with the outer surface 5*as* of the part of the thermal spray layer 5 located on the side surface 3*as* of the flange portion 3*a*. Herein, an inside diameter d of the seat portion 20*e* of the metal shell 20 (i.e. an inside diameter of a part of the metal shell 20 located rear of the seat portion 20*e*) is slightly made larger than an outside diameter of the flange portion 3*a* so that the gas sensor element 3 including the flange portion 3*a* can be prevented from radial displacement relative to the metal shell 20. The radial space between the protector 200 and the metal shell 20 is preferably made smaller (that is, an outside diameter of the metal portion 202 of the protector 200 is preferably made closer to the inside diameter d of the seat portion 20*e* of the metal shell 20) so that, even when the protector 200 is placed on the seat portion 20*e*, the protector 200 can be prevented from radial displacement relative to the metal shell 20. For this reason, it is necessary that the corner 202*j* between the outer side surface 202*y* and front end-facing surface 202*f* of the metal portion 202 axially overlaps in position with or radially outwardly protrudes from the outer surface 5*as* of the part of the thermal spray layer 5 located on the side surface 3*as* of the flange portion 3*a*.

Further, the seat portion 20*e* of the metal shell 20 with which the metal portion 202 is brought into contact is formed to define a single tapered surface that is inclined (constricted) directly from the inner side surface of the metal shell 20 toward the front end side. This advantageously makes it possible to facilitate the production of the seat portion 20*e* of the metal shell 20. This also advantageously makes it possible, at the time of pressing the gas sensor element 3 toward the front end side by crimping the rear end portion of the metal shell 20, to eliminate the need to perform a plurality of pressing steps corresponding to the respective step surfaces of the metal shell and to press the gas sensor element 3 in one step for reduction of processing time. As the seat portion 20*e* is formed with one tapered surface, the front end-facing surface 202*f* of the metal portion 202 is brought into contact with the seat portion 20*e*.

When the seat portion 20*e* is formed with one tapered surface as mentioned above, the metal portion 202 is deformed along the seat portion 20*e* such that a rear end-facing surface 202*r* of the metal portion 202 becomes flat and extends substantially along a straight line L as viewed in cross section. Thus, a part of the thermal spray layer 5 located in the vicinity of the corner 3*ac* between the front end-facing surface 3*af* and side surface 3*ac* of the flange portion 3*a* comes into contact with the metal portion 202 in the case where the front end-facing surface 3*af* of the flange portion 3*a* is formed into a flat shape. There is a possibility of separation of the thermal spray layer 5 from the side surface 3*as* of the flange portion 3*a* when crimping stress is exerted on the part of the thermal spray layer 5 located on the side surface 3*as* of the flange portion 3*a* in a direction along the side surface 3*as* of the flange portion 3*a* (i.e. in the direction of the axis O) under the above state. In view of such a problem, the front end-facing surface 3*af* and side surface 3*as* of the flange portion 3*a* are connected by a curved surface (that is, the corner 3*ac* is rounded off) such that the part of the thermal spray layer 5 located in the vicinity of the corner 3*ac* is axially spaced apart from the metal portion 202 so as to leave a gap G between the part of the thermal spray layer 5 located in the vicinity of the corner 3*ac* and the metal portion 202 as shown in FIG. 4 in the first embodiment. This makes it possible to keep the metal portion 202 from contact with the part of the thermal spray layer 5 located in the vicinity of the corner 3*ac* and prevent separation of the thermal spray layer 5 from the side surface 3*as* of the flange portion 3*a* even when crimping stress is exerted on the part of the thermal stray layer 5 located on the side surface 3*as* of the flange portion 3*a* in the direction along the side surface 3*as* of the flange portion 3*a*. On the other hand, the rear end-facing surface 202*r* of the metal portion 202 is brought into contact with an outer surface 5*af* of the part of the thermal spray layer 5 located on the front end-facing surface 3*af* of the flange portion 3*a* at a position radially inside the side surface 3*as* of the flange portion 3*a*. As crimping stress is exerted on the part of the thermal spray layer 5 located on the front end-facing surface 3*af* of the flange portion 3*a* in a direction intersecting the front end-facing surface 3*af* of the flange portion 3*a* (as compression stress along the lamination direction of the thermal spray layer 5), there does not occur a separation at the interface between the thermal spray layer 5 and the front end-facing surface 3*af* of the flange portion 3*a*.

For the purpose of minimizing the stress load exerted on the part of the thermal spray layer 5 located in the vicinity of the corner 3*ac*, it is preferable that the metal portion 202 is shaped in advance to substantially fit with the seat portion 20*e* although the metal portion 202 of the protector 200 can be first formed into a flat shape, placed on the seat portion 203, and then, deformed into a tapered shape by crimping the rear end portion of the metal shell 20 and pressing the gas sensor element 3 toward the front end side.

The element body 3*s* can be formed into a general shape with the use of a mold and then finished by grinding with the use of a grindstone. At this time, it is feasible to round off the corner 3*ac* by adjusting the cross-sectional shape of the grindstone for the formation of the corner 3*ac*.

Figure 5:
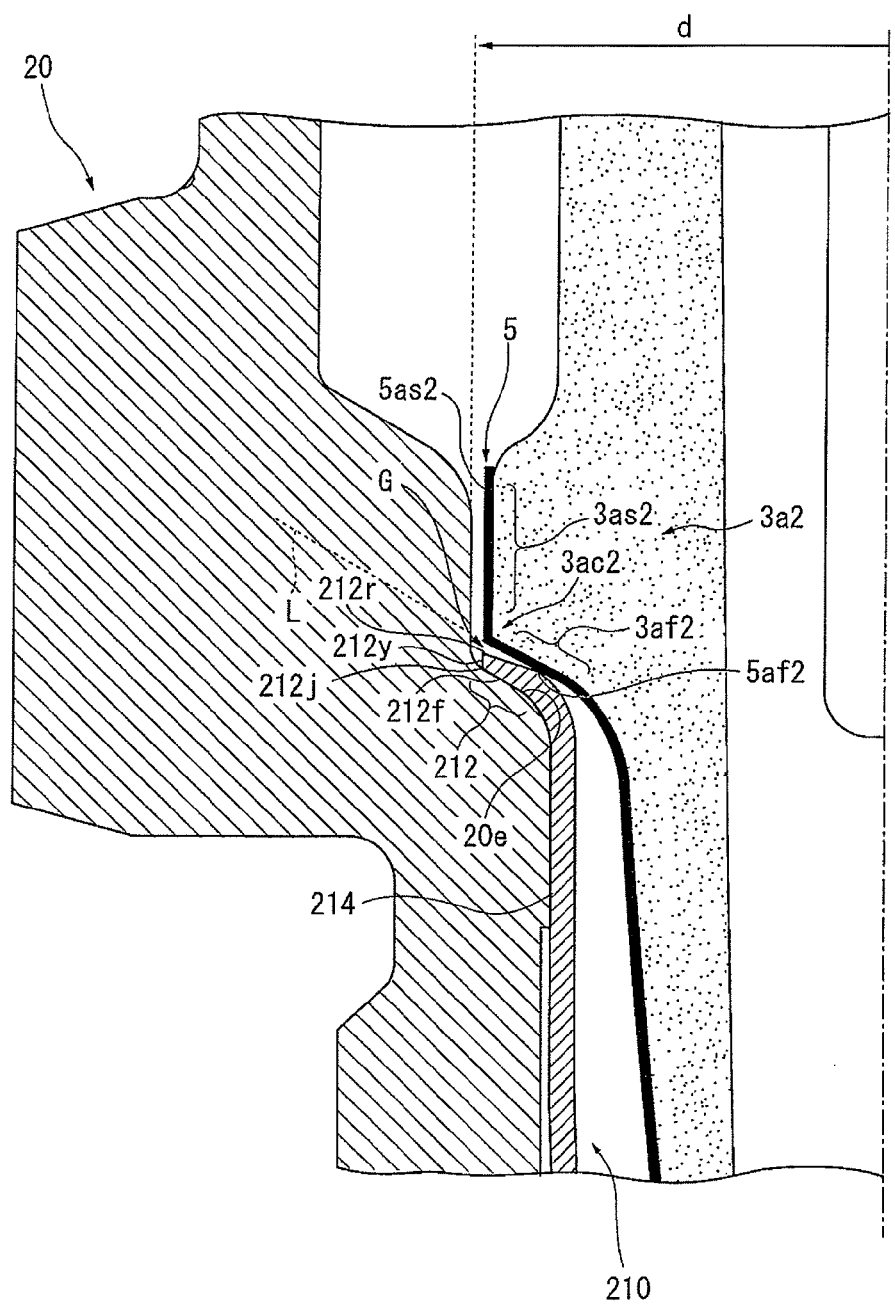
FIG. 5 is a schematic view showing a modified example of the metal portion of FIG. 4.

FIG. 5 is a schematic view showing a modified example of the protector 202 of FIG. 4. The configurations of any parts/portions other than a metal portion 212 of a protector 210 and a flange portion 3*a*2 of a gas sensor element 3 in FIG. 5 are the same as those of the gas sensor 100 of the first embodiment. As shown in FIG. 5, the metal portion 212 of the protector 210 is tapered and constricted toward the front end side and brought into contact with the seat portion 20*e*. The protector 210 also has a cylindrical protector portion 214 formed integral with the metal portion 212 so as to extend from a front end of the metal portion 212 toward the front end side.

In this example, an outer side surface 212*y* of the metal portion 212 of the protector 210 axially overlaps in position with an outer surface 5*as*2 of a part of the thermal spray layer 5 located on a side surface 3*as*2 of the flange portion 3*a*2 (that is, the outer side surface 212*y* of the metal portion 212 and the outer surface 5*as*2 of the thermal spray layer 5 are radially in the same position). In other words, a corner 212*j* connecting the outer side surface 212*y* and front end-facing surface 212*f* of the metal portion 212 axially overlaps in position with the outer surface 5*as*2 of the part of the thermal spray layer 5 located on the side surface 3*as*2 of the flange portion 3*a*2. Herein, an inside diameter d of the seat portion 20*e* of the metal shell 20 (i.e. an inside diameter of a part of the metal shell 20 located rear of the seat portion 20*e*) is slightly made larger than an outside diameter of the flange portion 3*a*2 so that the gas sensor element 3 including the flange portion 3*a*2 can be prevented from radial displacement relative to the metal shell 20. The radial space between the protector 210 and the metal shell 20 is preferably made smaller (i.e. the outside diameter of the metal portion 212 of the protector 210 is preferably made closer to the inside diameter d of the seat portion 20*e* of the metal shell 20) so that, even when the protector 210 is placed on the seat portion 20*e*, the protector 210 can be prevented from radial displacement relative to the metal shell 20. For this reason, the corner 212*j* between the outer side surface 212*y* and front end-facing surface 212*f* of the metal portion 202 axially overlaps in position with the outer surface 5as2 of the part of the thermal spray layer 5 located on the side surface 3as2 of the flange portion 3a.

Further, the seat portion 20e of the metal shell 20 with which the metal portion 212 is brought into contact is formed to define a single tapered surface that is inclined (constricted) directly from the inner side surface of the metal shell 20 toward the front end side. This advantageously makes it possible to facilitate the production of the seat portion 20e of the metal shell 20. This also advantageously makes it possible, at the time of pressing the gas sensor element toward the front end side by crimping the rear end portion of the metal shell 20, to eliminate the need to perform a plurality of pressing steps corresponding to the respective step surfaces of the metal shell and to press the gas sensor element 3 in one step for reduction of processing time. As the seat portion 20e is formed with one tapered surface, the front end-facing surface 212f of the metal portion 212 is brought into contact with the seat portion 20e.

As shown in FIG. 5, the side surface 3as2 and front end-facing surface 3af2 of the flange portion 3a2 are not connected by a curved surface but are directly connected to each other. The front end-facing surface 3af2 thus extends substantially along a straight line L as viewed in cross section in FIG. 5. When the metal portion 212 is deformed along the seat portion 20e such that a rear end-facing surface 212r of the metal portion 212 becomes flat as in the case of the metal portion 202 of the first embodiment (see FIG. 4) and extends along the straight line L, a part of the thermal spray layer 5 located in the vicinity of a corner 3ac2 between the front end-facing surface 3af2 and side surface 3as2 of the flange portion 3a2 comes into contact with the metal portion 212. In view of such a problem, the metal portion 212 is reduced in thickness toward the radially outside such that the part of the thermal spray layer 5 located in the vicinity of the corner 3ac2 is axially spaced apart from the metal portion 212 so as to leave a gap G between the part of the thermal spray layer 5 located in the vicinity of the corner 3ac2 and the metal portion 212. This makes it possible to keep the metal portion 212 from contact with the part of the thermal spray layer 5 located in the vicinity of the corner 3ac2 and prevent separation of the thermal spray layer 5 from the side surface 3as2 of the flange portion 3a2 even when crimping stress is exerted on the part of the thermal stray layer 5 located on the side surface 3as2 of the flange portion 3a2 in a direction along the side surface 3as2 of the flange portion 3a2. On the other hand, the rear end-facing surface 212r of the metal portion 212 is brought into contact with an outer surface 5af2 of the part of the thermal spray layer 5 located on the front end-facing surface 3af2 of the flange portion 3a2 at a position radially inside the side surface 3as2 of the flange portion 3a2. As crimping stress is exerted on the part of the thermal spray layer 5 located on the front end-facing surface 3af2 of the flange portion 3a2 in a direction intersecting the front end-facing surface 3af2 of the flange portion 3a2, there does not occur a separation at the interface between the thermal spray layer 5 and the front end-facing surface 3af2 of the flange portion 3a2.

Figure 6:
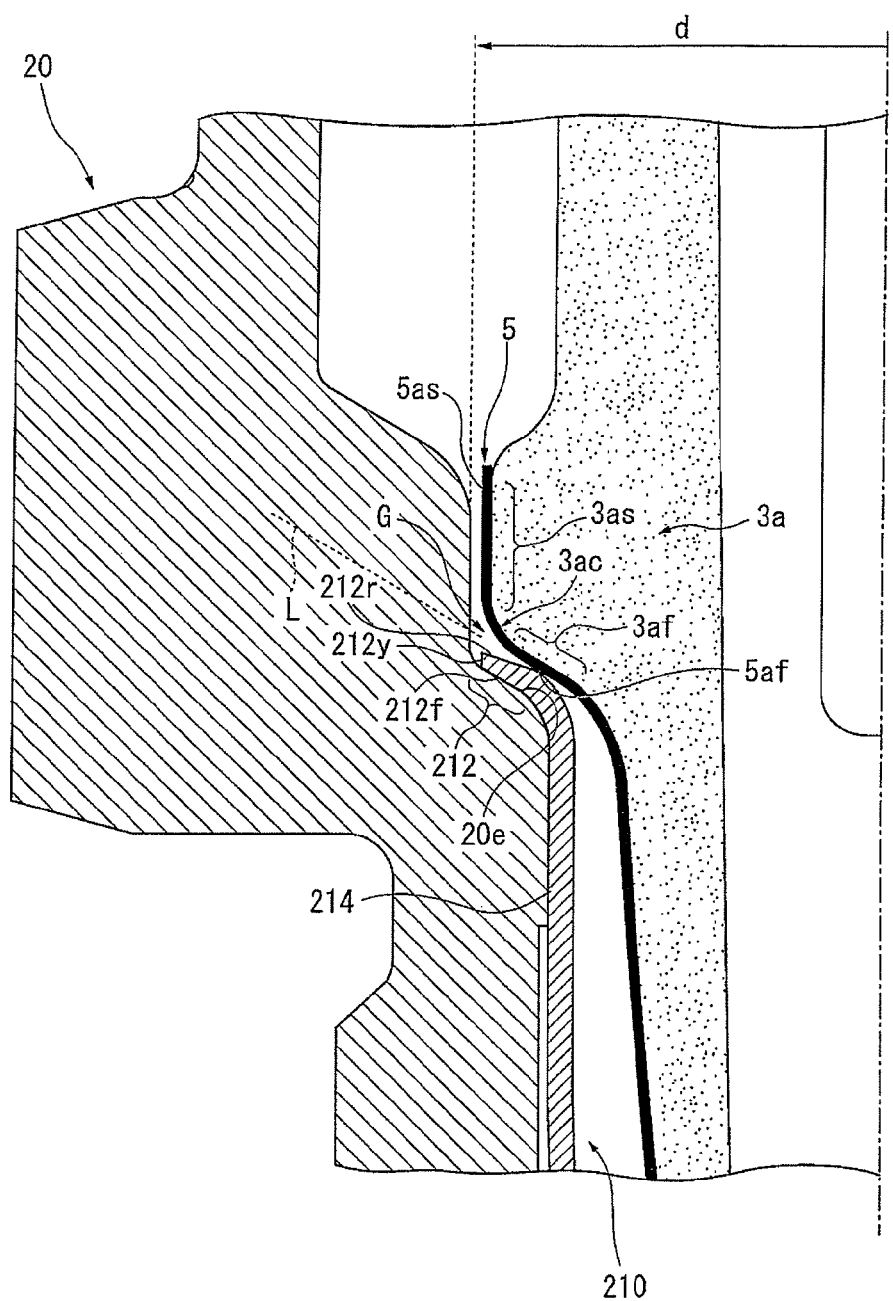
FIG. 6 is a schematic view showing another modified example of the metal portion of FIG. 4.

FIG. 6 is a schematic view showing another modified example of the protector 200 of FIG. 4. The configurations of any parts/portions other than a metal portion 212 of a protector 210 in FIG. 6 are the same as those of the gas sensor 100 of the first embodiment.

As shown in FIG. 6, the metal portion 212 is reduced in thickness toward the radially outside as in the case of the protector 210 of FIG. 5. Further, the front end-facing surface 3af and side surface 3as of the flange portion 3a are connected by a curved surface (that is, the corner 3ac is rounded off) as in the case of FIG. 4. The gap G between the part of the thermal spray layer 5 located in the vicinity of the corner 3ac and the metal portion 212 is thus made larger than those of FIGS. 4 and 5. This makes it possible to keep the metal portion 212 from contact with the part of the thermal spray layer 5 located in the vicinity of the corner 3ac and assuredly prevent separation of the thermal spray layer 5 from the side surface 3as of the flange portion 3a even when crimping stress is exerted on the part of the thermal stray layer 5 located on the side surface 3as of the flange portion 3a in a direction along the side surface 3as of the flange portion 3a.

Figure 7:
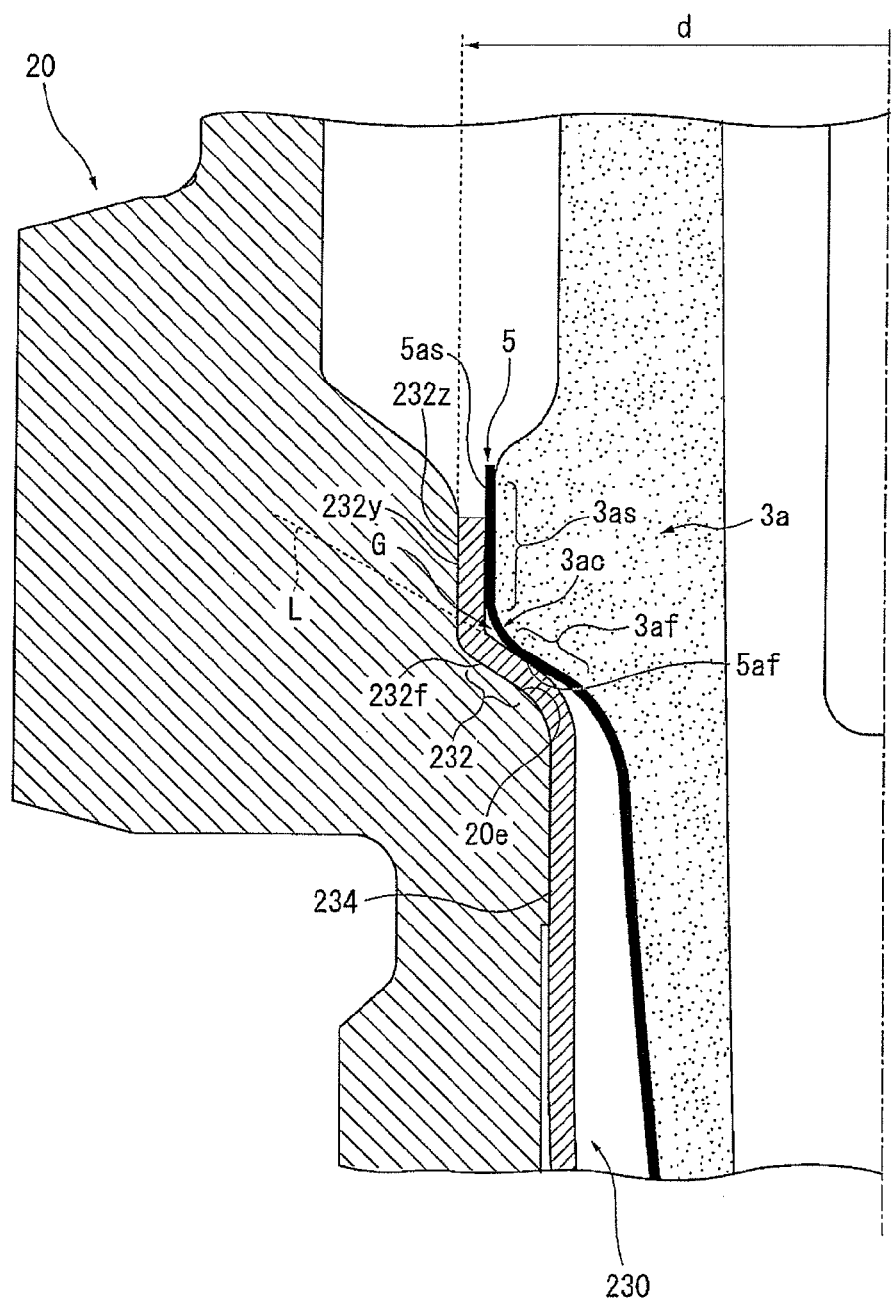
FIG. 7 is a schematic view showing still another modified example of the metal portion of FIG. 4.

FIG. 7 is a schematic view showing still another modified example of the protector 200 of FIG. 4. The configurations of any parts/portions other than a protector 230 in FIG. 7 are the same as those of the gas sensor 100 of the first embodiment.

As shown in FIG. 7, the protector 230 has a metal portion 232 and a protector portion 234 that are the same as those of the protector 200 of FIG. 4. The protector 230 also has a guide portion 232z formed integral with the metal portion 232 so as to extend in a cylindrical shape from the metal portion 232 toward the rear end side. There is a gap G left between the metal portion 232 and the part of the thermal spray layer 5 located in the vicinity of the corner 3ac as in the case of the protector 200 of FIG. 4.

In this example, an outside diameter of the guide portion 232z is made slightly smaller than an inside diameter d of the seat portion 20e of the metal shell 20. The guide portion 232z can thus fit with the inner side surface of the metal shell 20 and allow centering alignment of the protector 230 and the metal shell 20 at the time of placing the protector 230 into the metal shell 20 from the rear end side. In addition, the protector 230 can be held tightly in the metal shell 20 by arrangement of the guide portion 232z between the metal shell 20 and the side surface 3as of the flange portion 3a.

At the time of crimping the rear end portion of the metal shell 20 and pressing the gas sensor element 3 toward the front end side, the guide portion 232z may be brought into contact with the part of the thermal spray layer 5 located on the side surface 3as of the flange portion 3a. In this example, however, stress exerted by the guide portion 232z on the thermal pray layer 5 is sufficiently smaller than crimping stress exerted on the thermal spray layer 5 in the direction of the axis O. Under such small stress, there is no possibility of separation of the thermal spray layer 5 from the side surface 3as of the flange portion 3a.

Next, a gas sensor 110 according to a second embodiment of the present invention will be explained below with reference to FIGS. 8 to 10.

Figure 8:
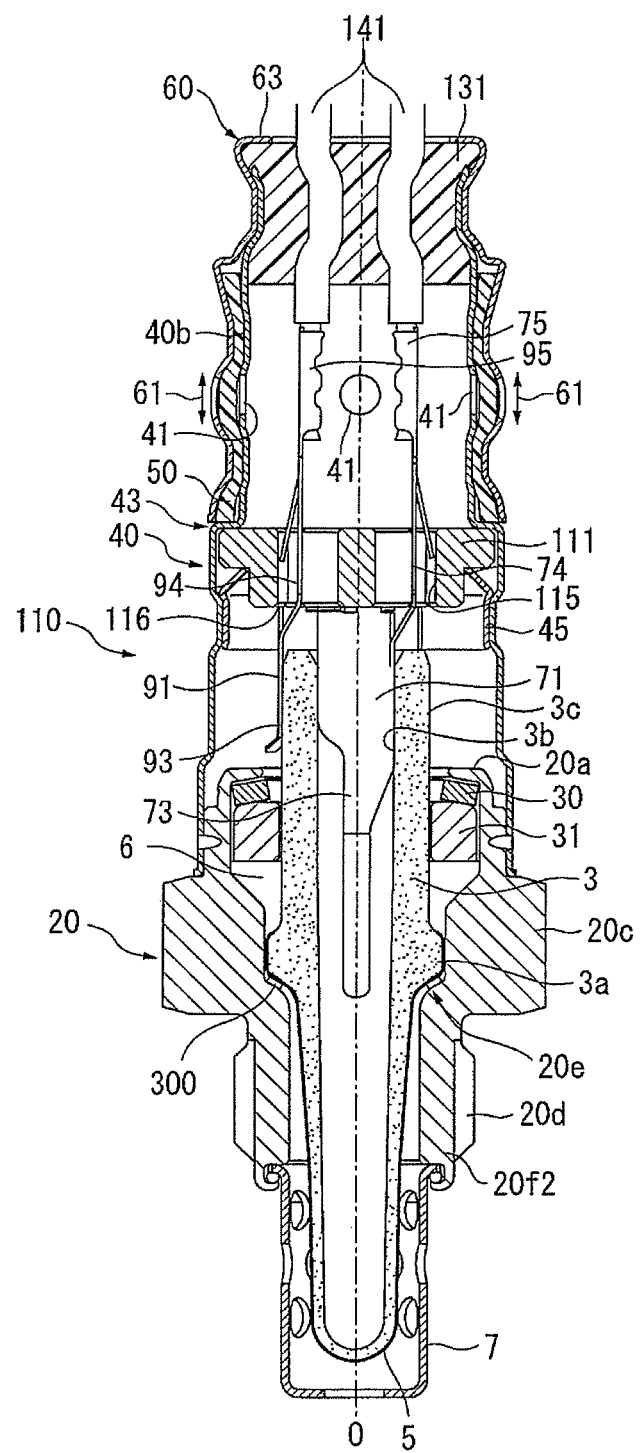
FIG. 8 is a cross-section view of a gas sensor, taken along the direction of an axis of the gas sensor, according to a second embodiment of the present invention.

FIG. 8 is a cross-section view of the gas sensor 110 according to the second embodiment, taken along the direction of an axis O of the gas sensor 110 and corresponding to the cross section of the gas sensor 100 of FIG. 1. The gas sensor 110 is the same in configuration as the gas sensor 100 of the first embodiment, except for a packing 300 (as the claimed metal portion), a front end portion 20f2 of a metal shell 20 and a protector member 7 formed as a separate part from the packing 300. An explanation of the same parts and portions of the gas sensor 110 as those of the gas sensor 100 will be thus omitted herefrom.

As shown in FIG. 8, the packing 300 is tapered and constricted toward the front end side and brought into contact with the seat portion 20e. In the second embodiment, the packing 300 is engaged between the flange portion 3a and the seat portion 20e.

The protector 7 is made of a metal material (such as stainless steel) in a cylindrical shape (as a separate part from the packing 300) and is fixed to the front end portion 20f2 of the metal shell 20 so as to cover a front end portion of the gas sensor element 3 protruding from the metal shell 3. Further, the protector member 7 has a plurality of holes formed therein to introduce the exhaust gas to the inside of the protector member 7.

Figure 9:
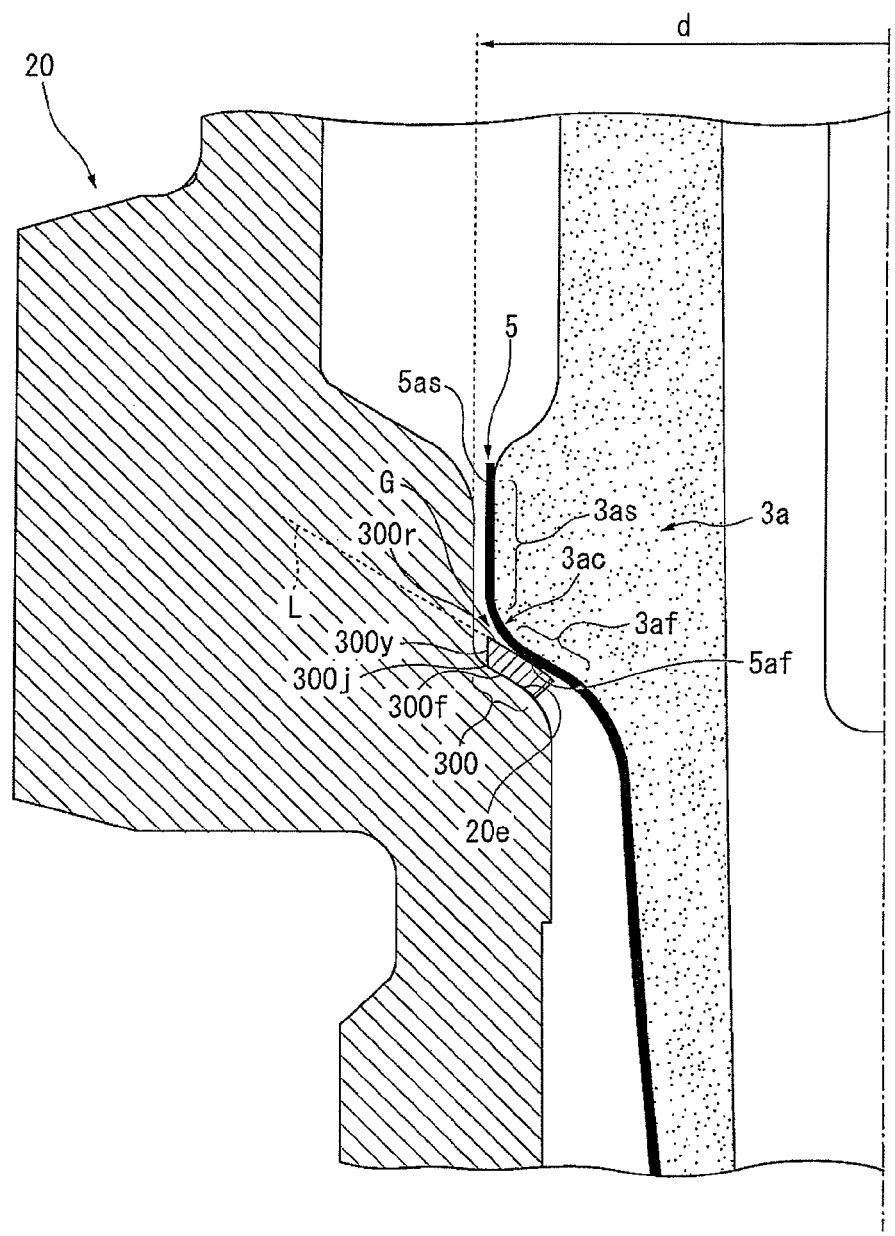
FIG. 9 is an enlarged view of part of FIG. 8, showing a packing in the gas sensor according to the second embodiment of the present invention.

FIG. 9 is a schematic enlarged view of part of FIG. 8. The packing 300 is the same in configuration as the protector 200 of the first embodiment (see FIG. 4), except for the shape of the packing 3 itself and the formation of no protector portion 204. Thus, a rear end-facing surface 300r of the packing 3 becomes flat along a straight line L as in the case of the protector 200 of the first embodiment. However, there is a gap G left between the part of the thermal spray layer 5 located in the vicinity of the corner 3ac and the packing 300 when the side and front end-facing surfaces 3as and 3af of the flange portion 3a are connected by a curved surface (that is, the corner 3ac is rounded off). This makes it possible to keep the packing 300 from contact with the part of the thermal spray layer 5 located in the vicinity of the corner 3ac and prevent separation of the thermal spray layer 5 from the side surface 3as of the flange portion 3a even when crimping stress is exerted on the part of the thermal stray layer 5 located on the side surface 3as of the flange portion 3a in a direction along the side surface 3as of the flange portion 3a. The rear end-facing surface 300r of the packing 300 is brought into contact with an outer surface 5af of the part of the thermal spray layer 5 located on the front end-facing surface 3af of the flange portion 3a at a position radially inside the side surface 3as of the flange portion 3a. An outer side surface 300y of the packing 300 is located such that a part of the outer side surface 300y radially outwardly protrudes from an outer surface 5as of the part of the thermal spray layer 5 located on the side surface 3as of the flange portion 3a and another part of the outer side surface 300y remains radially inside the outer surface 5as of the thermal spray layer 5. Namely, the outer side surface 300y of the packing 300 overlaps in position with the outer surface 5as of the part of the thermal spray layer 5 located on the side surface 3as of the flange portion 3a. Even in this configuration, it is less likely that the packing 300 will be radially displaced in position relative to the metal shell 20 when a corner 300j connecting the outer side surface 300y and front end-facing surface 300f of the packing 300 radially outwardly protrudes from the outer surface 5as of the part of the thermal spray layer 5 located on the side surface 3as of the flange portion 3a in the second embodiment. The packing 300 is brought at the front end-facing surface 300f thereof into contact with the seat portion 20e.

Figure 10:
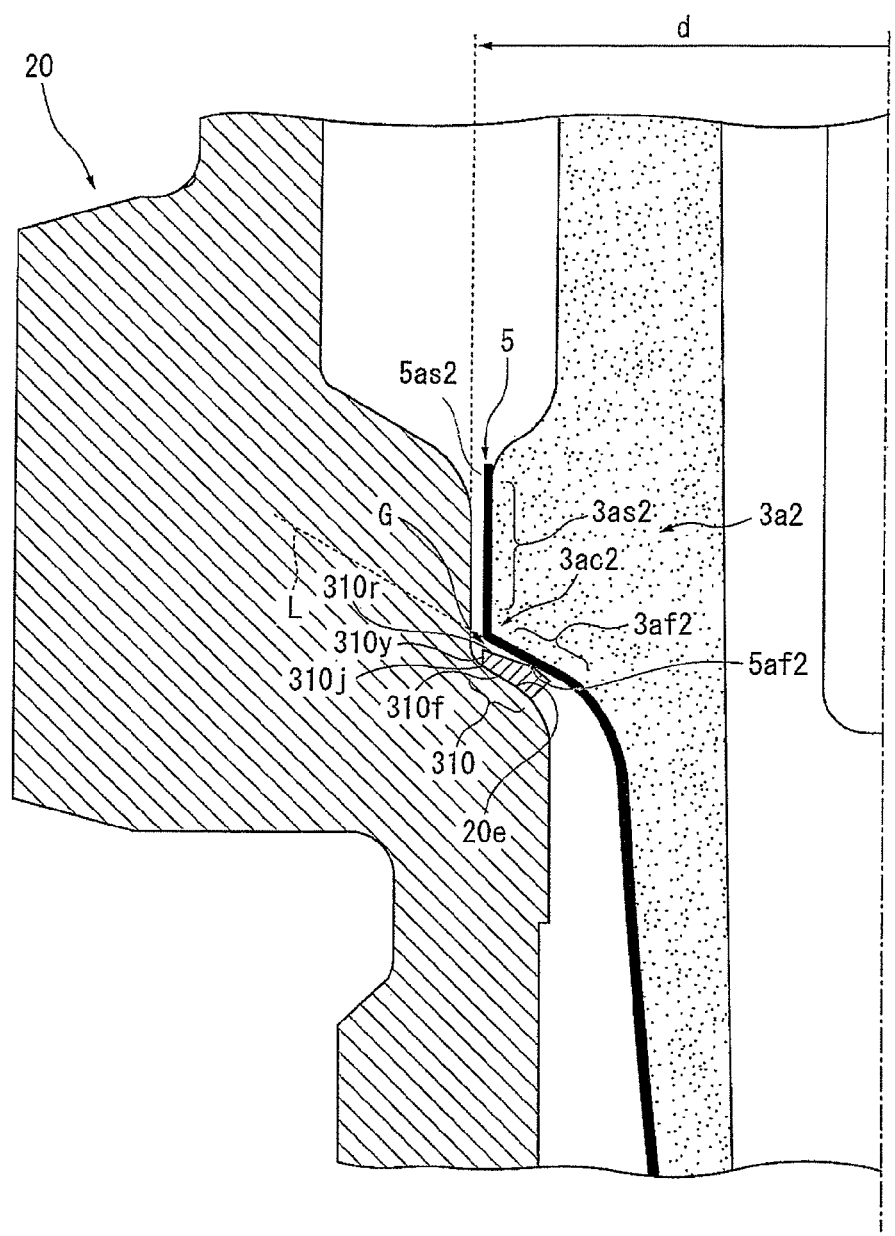
FIG. 10 is a schematic view showing a modified example of the packing of FIG. 9.

FIG. 10 is a schematic view showing a packing 310 as a modified example of the packing 300 of FIG. 9. The packing 310 of FIG. 10 is the same in configuration as the protector 210 of FIG. 5, except for the formation of no protector portion 214. Even though the side surface 3as2 and front end-facing surface 3af2 of the flange portion 3a2 are not connected by a curved surface, the packing 310 is reduced in thickness toward the radially outside, as in the case of the protector 210 of FIG. 5, so as to leave a gap G between the part of the thermal spray layer 5 located in the vicinity of the corner 3ac2 and the packing 310. This makes it possible to keep the packing 310 from contact with the part of the thermal spray layer 5 located in the vicinity of the corner 3ac2 and prevent separation of the thermal spray layer 5 from the side surface 3as2 of the flange portion 3a2 even when crimping stress is exerted on the part of the thermal stray layer 5 located on the side surface 3as2 of the flange portion 3a2 in a direction along the side surface 3as2 of the flange portion 3a2. On the other hand, a rear end-facing surface 310r of the packing 310 is brought into contact with an outer surface 5af2 of the part of the thermal spray layer 5 located on the front end-facing surface 3af2 of the flange portion 3a2 at a position radially inside the side surface 3as2 of the flange portion 3a2. An outer side surface 310y of the packing 310 is located such that a part of the outer side surface 310y radially outwardly protrudes from an outer surface 5as2 of the part of the thermal spray layer 5 located on the side surface 3as2 of the flange portion 3a2 and another part of the outer side surface 310y remains radially inside the outer surface 5as2 of the thermal spray layer 5. Namely, the outer side surface 310y of the packing 300 overlaps in position with the outer surface 5as2 of the part of the thermal spray layer 5 located on the side surface 3as2 of the flange portion 3a2. Even in this configuration, it is less likely that the packing 310 will be radially displaced in position relative to the metal shell 20 when a corner 310j connecting the outer side surface 310y and front end-facing surface 310f of the packing 310 radially outwardly protrudes from the outer surface 5as2 of the part of the thermal spray layer 5 located on the side surface 3as2 of the flange portion 3a2. The packing 310 is brought at the front end-facing surface 310f thereof into contact with the seat portion 20e.

In the second embodiment, it is feasible to increase the gap G by reducing the thickness of the packing 310 toward the radially outside and connecting the side surface 3as and front end-facing surface 3af of the flange portion 3a by a curved surface as in the case of the first embodiment (the example of FIG. 6). It is also feasible in the second embodiment to form a guide portion integral with the packing 300 such that the guide portion extends in a cylindrical shape from the packing 300 toward the rear end side as in the case of the first embodiment (the example of FIG. 7).

Figure 11:
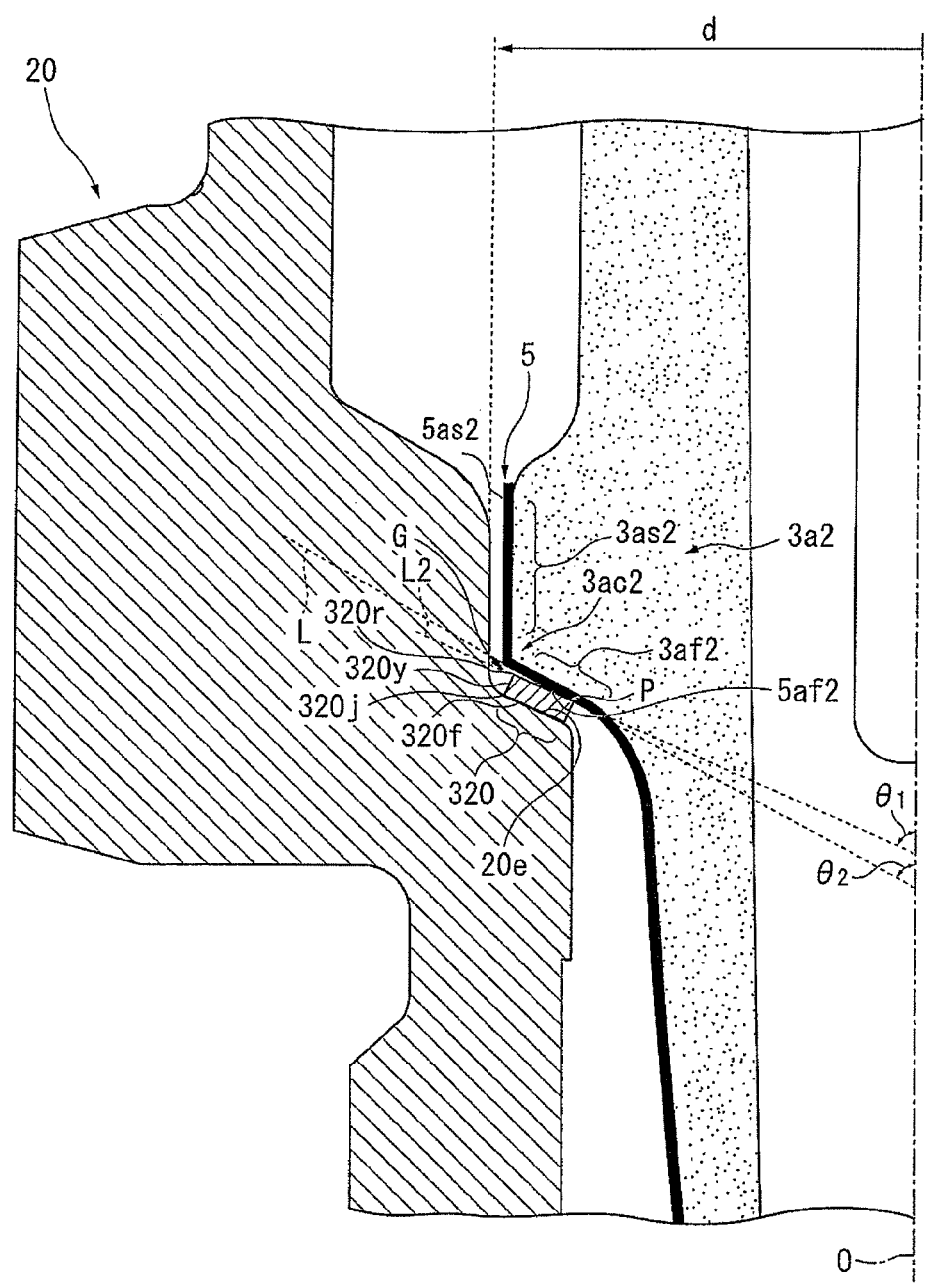
FIG. 11 is a schematic view showing another modified example of the packing of FIG. 9.
Figure 12:
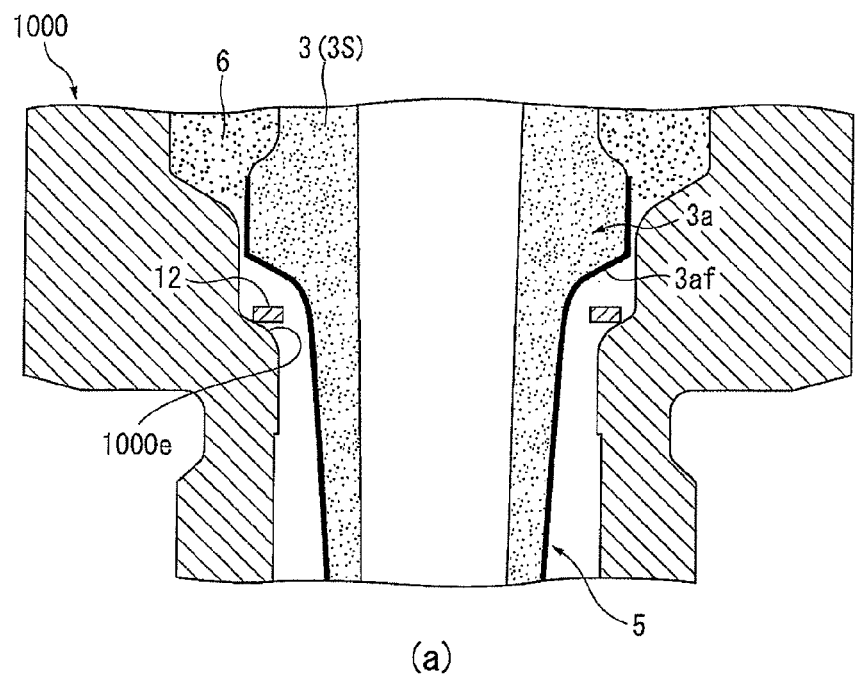
FIG. 12 is a schematic view showing a state where a metal packing is arranged between a gas sensor element and a metal shell in a conventional gas sensor.
Figure 12:
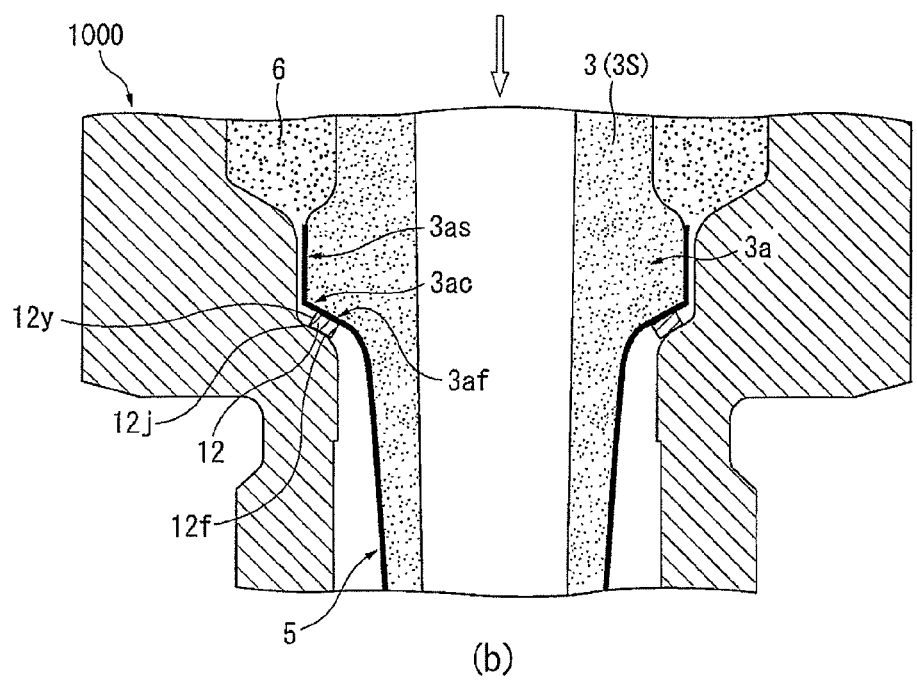

FIG. 11 is a schematic view showing a packing 320 as another modified example of the packing 300 of FIG. 9. As shown in FIG. 11, the packing 320 has a uniform thickness and an ordinary shape such that a radially outer side surface 320y of the packing 320 is at a right angle relative to a rear end-facing surface 320r of the packing 320. The flange portion 3a2 is the same in shape as that of FIG. 5 such that the front end-facing surface 3af2 of the flange portion 3a2 is flat and extends substantially along a straight line L as viewed in cross section in FIG. 11. The straight line L (the outer surface 5af2 of the thermal spray layer) forms an angle $\theta_2$ relative to the direction of the axis O. Herein, an angle formed between the seat portion 20e of the metal shell and the direction of the axis O in FIG. 11 is made larger than an angle formed between the seat portion 20e of the metal shell and the direction of the axis O in FIG. 9.

On the other hand, a straight line $L_2$ parallel to the rear end-facing surface 320r of the packing 320 forms an angle $\theta_1$ relative to the direction of the axis O. In this example, the angles $\theta_1$ and $\theta_2$ are set to satisfy the condition of $\theta_1 > \theta_2$.

Thus, the part of the thermal spray layer 5 located in the vicinity of the corner 3ac2 is axially spaced apart from the packing 320 so as to leave a gap G between the part of the thermal spray layer 5 located in the vicinity of the corner 3ac2 and the packing 320 even when the rear end-facing surface 320r of the packing 320 is made flat as in the case of the metal portion 202 of the first embodiment (see FIG. 4). This makes it possible to keep the packing 320 from contact with the part of the thermal spray layer 5 located in the vicinity of the corner 3ac2 and prevent separation of the thermal spray layer 5 from the side surface 3as2 of the flange portion 3a2 even when crimping stress is exerted on the part of the thermal stray layer 5 located on the side surface 3as2 of the flange portion 3a2 in a direction along the side surface 3as2 of the flange portion 3a2. On the other hand, the rear end-facing surface 320r of the packing 320 is brought into contact with an outer surface 5*af*2 of the part of the thermal spray layer 5 located on the front end-facing surface 3*af*2 of the flange portion 3*a*2 at a position radially inside the side surface 3*as*2 of the flange portion 3*a*2. An outer side surface 320*y* of the packing 320 is located such that a part of the outer side surface 320*y* radially outwardly protrudes from an outer surface 5*as*2 of the part of the thermal spray layer 5 located on the side surface 3*as*2 of the flange portion 3*a*2 and another part of the outer side surface 320*y* remains radially inside the outer surface 5*as*2 of the thermal spray layer 5. Namely, the outer side surface 320*y* of the packing 320 overlaps in position with the outer surface 5*as*2 of the part of the thermal spray layer 5 located on the side surface 3*as*2 of the flange portion 3*a*2. Even in this configuration, it is less likely that the packing 320 will be radially displaced in position relative to the metal shell 20 when a corner 320*j* connecting the outer side surface 320*y* and front end-facing surface 320*f* of the packing 320 radially outwardly protrudes from the outer surface 5*as*2 of the part of the thermal spray layer 5 located on the side surface 3*as*2 of the flange portion 3*a*2. The packing 320 is brought at the front end-facing surface 320*f* thereof into contact with the seat portion 20*e*.

When the outer surface 5*af*2 of the thermal spray layer 5 is pressed against the rear end-facing surface 320*r* of the packing 320, the rear end-facing surface 320*r* is deformed at a contact point P so as to fit with the outer surface 5*af*2. In this state, the rear end-facing surface 320*r* and the outer surface 5*af*2 are in the same plane at the contact point P so that the above-defined angles $\theta_1$ and $\theta_2$ becomes equal to each other ($\theta_1 = \theta_2$). The angle $\theta_1$ is thus defined in a region radially outside the contact point P. The angle $\theta_1$ defined in the region radially outside the contact point P corresponds to the claimed angle formed between the rear end-facing surface of the metal portion and the axis direction in the region radially outside the contact of the metal portion and the outer surface of the thermal stray layer.

In the example of FIG. 11, the packing 320 is of ordinary shape. The use of such a packing 320 leads to reduction in parts cost. The packing 320 is not however limited to the ordinary shape. It is feasible to reduce the thickness of the packing 320 toward the radially outside as in the case of the packing 310 of FIG. 10.

Although the present invention has been described above with reference to the specific exemplary embodiments, the present invention is not limited to the above-described exemplary embodiments. Various modifications and variations of the embodiment described above will occur within the scope of the present invention.

For example, the side surface 3*as* and front end-facing surface 3*af* of the flange portion 3*a* may alternatively be connected by a plain surface (that is, the corner 3*ac* may be chamfered at a given angle relative to the front end-facing surface 3*af* of the flange portion) although the side surface 3*as* and front end-facing surface 3*af* of the flange portion 3*a* are connected by a curved surface (that is, the corner 3*ac* is rounded off) in the first embodiment as shown in FIG. 4, 6 or 7 and in the second embodiment as shown in FIG. 9.

Although the outer electrode 3*c* is formed on the entire part of the gas sensor element 3 located front of the flange portion 3*a* as shown in FIG. 2, the outer electrode 3*c* may alternatively be formed on some part of the gas sensor element 3 located front of the flange portion 3*a*.

DESCRIPTION OF REFERENCE NUMERALS

3: Gas sensor element
3*a*, 3*a*2: Flange portion
3*af*, 3*af*2: Front end-facing surface of flange portion
3*as*, 3*af*2: Side surface of flange portion
3*ac*, 3*as*2: Corner of flange portion
3*c* (3*cs*): Outer electrode
3*s*: Element body
5: Thermal spray layer
5*as*, 5*af*, 5*af*2: Outer surface of thermal spray layer
100, 110: Gas sensor
20: Metal shell
20*e*: Seat portion of metal shell
200, 210, 230, 300, 310, 320: Protector (packing)
202, 212, 232, 300, 310, 320: Metal portion
202*y*, 212*y*, 232*y*, 300*y*, 310*y*, 320*y*: Outer side surface of metal portion
202*f*, 212*f*, 232*f*, 300*f*, 310*f*, 320*f*: Front end-facing surface of metal portion
202*j*, 212*j*, 300*j*, 310*j*, 320*j*: Corner between outer side and front end-facing surfaces of metal portion
202*r*, 212*r*, 300*r*, 310*r*, 320*r*: Rear end-facing surface of metal portion
204, 214, 234: Protector portion
O: Axis
G: Gap (space)
$\theta_1$: Angle between rear end-facing surface of metal portion and direction of axis
$\theta_2$: Angle between outer surface of thermal spray layer and direction of axis

The invention claimed is:

1. A gas sensor, comprising:
a gas sensor element extending in an axis direction of the gas sensor and including a bottomed cylindrical element body and an outer electrode, the element body being exposed to a gas under measurement at a front end side thereof and opened at a rear end side thereof and having a radially outwardly protruding flange portion, the outer electrode being formed on an outer surface of a front end portion of the element body located front of the flange portion;
a cylindrical metal shell radially outwardly surrounding the gas sensor element and having, on an inner surface thereof, a seat portion tapered and inclined toward the front end side so as to face a front end-facing surface of the flange portion; and
an annular metal portion arranged between the front end-facing surface of the flange portion and the seat portion, the metal portion having a front end-facing surface, a rear end-facing surface, a radially outer side surface and a corner connecting the front end-facing surface and the radially outer side surface,
wherein the gas sensor further comprises a porous thermal spray layer formed on a region from the front end portion of the element body via the front end-facing surface to at least a side surface of the flange portion so as to cover the outer electrode; and
wherein, when viewed in cross section along the axis direction, the metal portion is formed such that: the corner of the metal portion axially overlaps in position with or radially outwardly protrudes from an outer surface of a part of the thermal spray layer located on the side surface of the flange portion, such that the corner of the metal portion is brought into direct contact with the seat portion, and such that the rear end-facing surface of the metal portion is brought into contact with an outer surface of a part of the thermal spray layer located on the front end-facing surface of the flange portion at a position radially inside the side surface of the flange portion.

2. The gas sensor according to claim 1, wherein the side surface of the flange portion and the front-facing surface of the flange portion are connected by a curved surface or a plain surface.

3. The gas sensor according to claim 1, wherein, in a region radially outside the contact of the metal portion and the outer surface of the thermal spray layer, an angle formed between the rear end-facing surface of the metal portion and the axis direction is larger than an angle formed between the outer surface of the thermal spray layer and the axis direction.

4. The gas sensor according to claim 1, wherein the metal portion is reduced in thickness toward the radially outside.

5. The gas sensor according to claim 1, wherein the gas sensor further comprises a protector portion formed integral with the metal portion so as to extend from the metal portion toward the front end side and accommodate therein the gas sensor element.

* * * * *